United States Patent [19]

Boiteau et al.

[11] Patent Number: 5,003,657
[45] Date of Patent: Apr. 2, 1991

[54] DEVICE FOR UNBLOCKING INTUBATION TUBES AND TRACHEOTOMY CANNULAS IN VIVO

[75] Inventors: Richard Boiteau, Paris; Denis Labayle; Alain Tenaillon, both of L'Hay-les-Roses, all of France

[73] Assignee: Medipro, Paris, France

[21] Appl. No.: 348,584

[22] PCT Filed: Jul. 8, 1988

[86] PCT No.: PCT/FR88/00364
  § 371 Date: Mar. 6, 1989
  § 102(e) Date: Mar. 6, 1989

[87] PCT Pub. No.: WO89/00058
  PCT Pub. Date: Jan. 12, 1989

[30] Foreign Application Priority Data

Jul. 8, 1987 [FR] France .................. 87 09671

[51] Int. Cl.⁵ ................................. B08B 9/02
[52] U.S. Cl. ................. 15/104.33; 15/104.16; 15/104.18; 604/158
[58] Field of Search ........... 15/104.32, 104.33, 104.16, 15/104.18; 604/54, 158

[56] References Cited

U.S. PATENT DOCUMENTS

| 1,858,176 | 5/1932 | Webb | 15/104.33 |
| 2,118,631 | 5/1938 | Wappler | 15/104.33 |
| 2,739,585 | 3/1956 | Ayre | 15/104.33 |
| 4,006,508 | 2/1977 | Brown | 15/104.33 |

Primary Examiner—Edward L. Roberts
Attorney, Agent, or Firm—Young & Thompson

[57] ABSTRACT

A device for unblocking intubation tubes in intubated patients and tracheotomy cannulas in tracheotomized patients comprises two elements which are introduced into the intubation tube or tracheotomy cannula by their distal end, namely a flexible rod (1) rounded at its distal end (2) provided with a collapsible system (3) near its distal end, and provided with a projection (5) at the other end to permit manipulation, and a flexible tube (4) provide with a reference stop (6) at its proximal end, into which the rod (1) is inserted and in which it can slide. The collapsible system (3) is collapsed in the flexible tube (4) and the sliding of the central rod (1) inside the flexible tube (4) after the introduction of device into the intubation tube or into the tracheotomy cannula releases the collapsible system (3), which sweeps the tube and the tracheotomy cannula as the device is withdrawn. This device may be sterile and disposable. Its use is recommended one to four times daily.

12 Claims, 3 Drawing Sheets

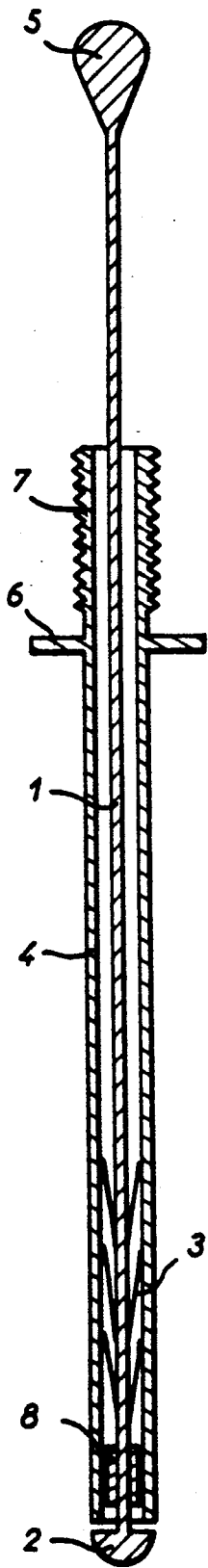
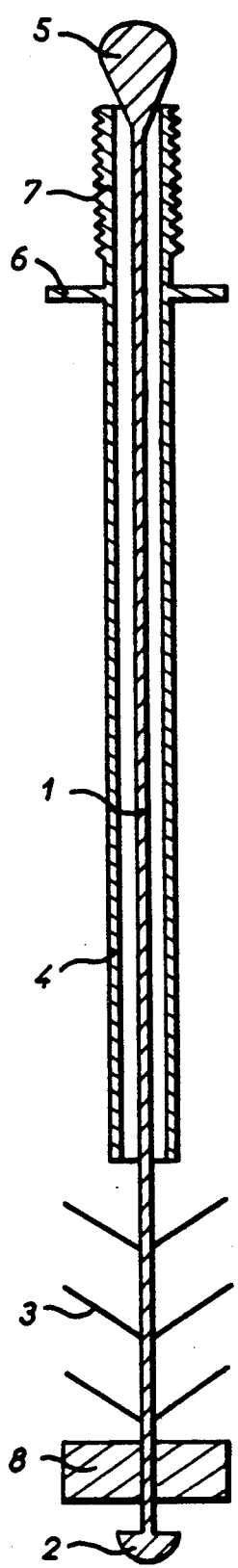
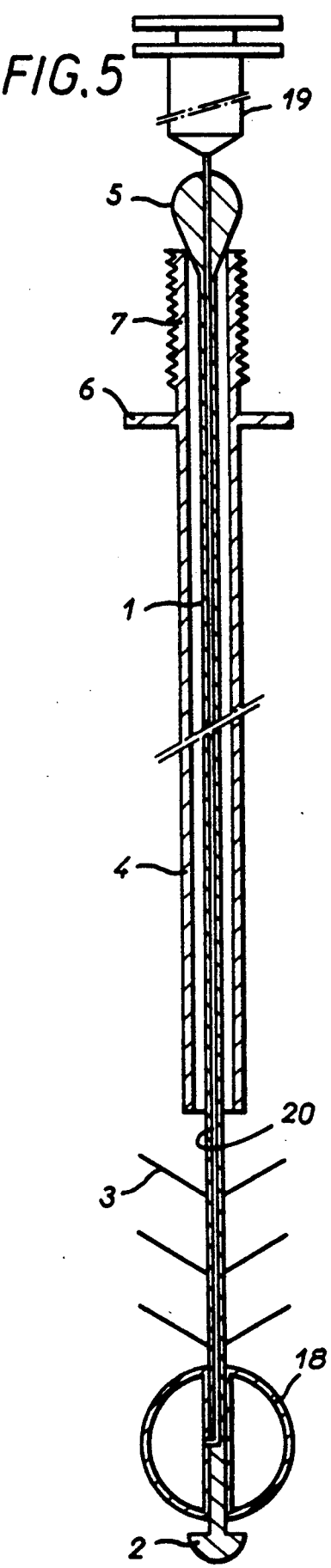

DEVICE FOR UNBLOCKING INTUBATION TUBES AND TRACHEOTOMY CANNULAS IN VIVO

The present invention relates to a device for preventing, by brushing, the blocking of intubation tubes in intubated patients and tracheotomy cannulas in tracheotomized patients.

Usually, in intubated or tracheotomized patients, the insertion of a tracheal aspiration tube permits aspiration of the patient's bronchial secretions and verification of the permeability of the intubation tube or of the tracheotomy cannula, but it does not prevent the gradual or sudden blocking of the tube or the cannula by organic deposits. The consequences of this blocking are numerous and sometimes serious, and they can put the patient's life at risk.

The device according to the invention enables this drawback to be remedied. It comprises two elements each having a distal end introduced into the intubation tube or the tracheotomy cannula and a proximal end manipulated by the operator.

The first element is a flexible, central rod the distal end of which is rounded so as to be non-traumatic. All around the rod near the distal end is inserted a collapsible system that is to enable the tube to be cleaned by brushing. The proximal portion of the rod ends in a projection enabling the rod to be firmly grasped.

The second element is a flexible tube in which the first element is inserted and in which it can slide. The tube is shorter than the rod itself. The outside diameter of the tube is similar for diameters of the different tubes or cannulas to permit ease of insertion. The overall length of the device depends on the length of the intubation tubes or tracheotomy cannulas. It is always substantially greater than that of the tube or the cannula. The collapsible system inserted on the rod is collapsed inside the tube. The distal end of the tube abuts against the rounded distal end of the rod.

The whole of the device is introduced into the intubation tube or the tracheotomy cannula by the distal end. A reference stop on the tube enables the device to be positioned in relation to the distal end of the intubation tube or the tracheotomy cannula.

The proximal end of the tube is treated to ensure that it can be securely gripped. By sliding the tube over the rod so as to block it against the projection of the rod serving as a handle, the user releases the system collapsed in the tube. He then withdraws the device and the released system brushes the intubation tube or the tracheotomy cannula.

According to a preferred form of embodiment, the collapsible system is constituted by bristles inserted all around the central rod. A small cylinder of foam is fixed to the distal end of the rod, between the bristles and the rounded portion, also collapsed inside the tube. Released at the same time as the bristles, it enables the debris dislodged by the bristles to be collected. This foam cylinder is optional.

According to an alternative embodiment, it is an inflatable balloon that is placed between the rounded distal end and the bristles on the rod. This balloon can be inflated by means of a syringe via a channel included in the rod.

According to another alternative embodiment, the collapsible system is constituted by strips of plastic inserted on the rod; again, it is possible to place a foam cylinder or an inflatable balloon between the rounded distal end and the strips.

The characteristics and advantages of the invention will become apparent, moreover, from the following description given by way of example with reference to the accompanying drawings.

FIG. 1 is a cross section of an embodiment of the device with tube/cannula cleaning means in a retracted configuration;

FIG. 2 is a view similar to that of FIG. 1, with the tube/cannula cleaning means in a deployed position;

FIG. 5 is a view similar to that of FIG. 2 illustrating another embodiment in which an inflatable balloon is provided on the rod.

Figure 3:
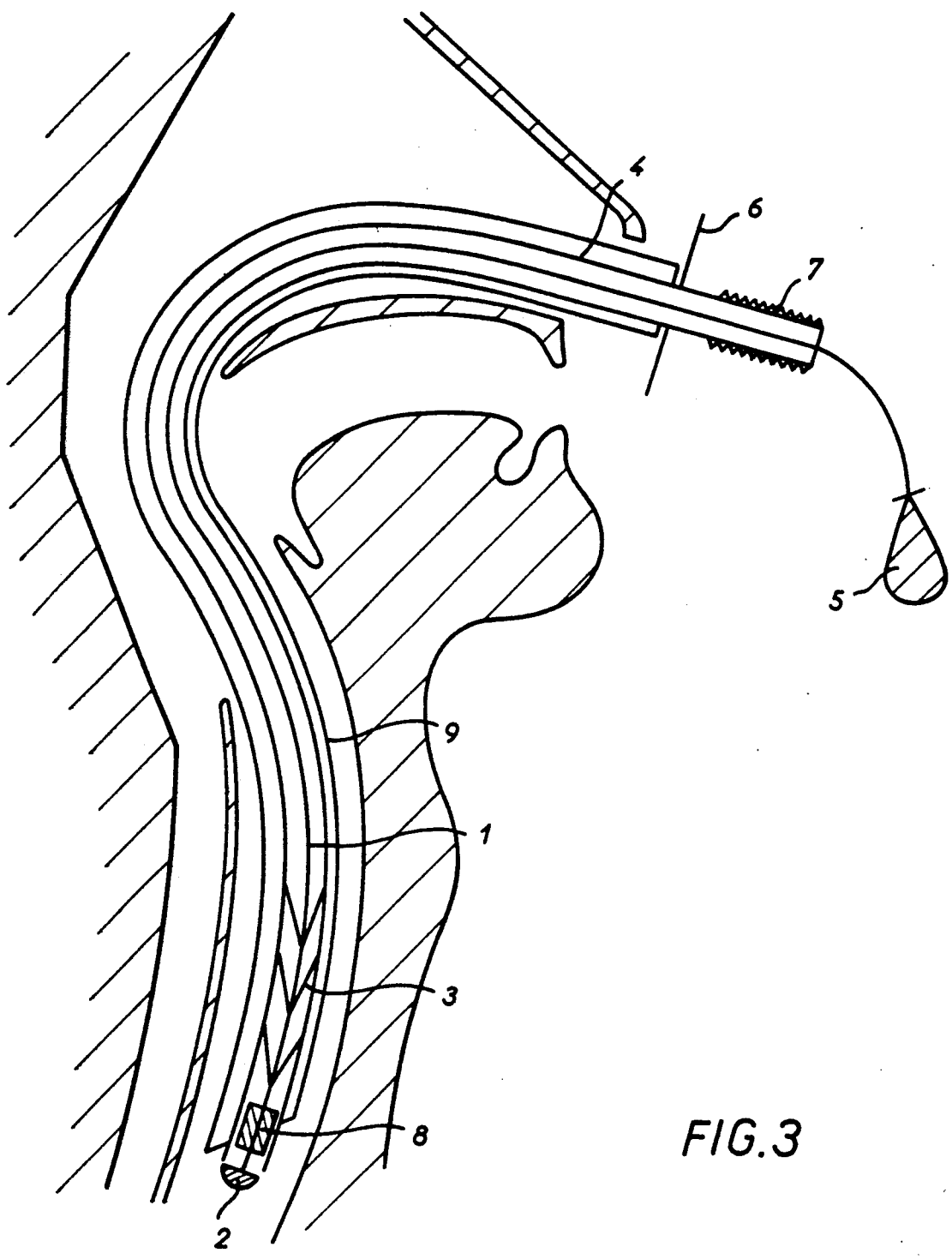
FIG. 3 is a view of the define in place in an intubated patient, with the tube/cannula cleaning means in the retracted configuration.

The device represented in FIG. 1 comprises, on one hand, a flexible central rod (1) whose distal end (2) is rounded, a collapsible or retractable system (3) fitted all around the rod in the vicinity of the distal end, a collapsed foam cylinder (8) fitted on the rod (1) between the collapsible system (3) and the rounded distal end (2) and a projection (5) terminating the proximal end of the rod (1) and permitting its manipulation. The device represented in FIG. 1 further comprises a flexible tube (4) in which the rod (1) is inserted and in which it can slide; the collapsible system (3) and the foam cylinder (8) are collapsed inside the tube (4). The distal end of the tube (4) abuts against the rounded distal end (2) of the rod (1). The tube (4) is fitted with a reference stop (6) enabling the device to be positioned in relation to the distal end of the intubation tube or the tracheotomy cannula. The proximal end of the tube (4) is threaded at (7) to ensure a firm grip on the tube.

FIG. 2 is a cross-section of the same embodiment of the device as in FIG. 1 after the tube (4) has been slid over the rod (1). The proximal end of the tube (4) is then blocked against the projection (5). The collapsible system (3) and the foam cylinder (8) are released.

FIG. 3 is a cross-section of the same embodiment of the device as in FIGS. 1 and 2 in place in an intubated patient after introduction into the intubation tube 9 by the operator and before sliding the tube over the rod. The configuration of the device is that of FIG. 1. The reference stop (6) blocked against the proximal end of the intubation tube enables the distal end (2) of the device to be positioned correctly in relation to the end of the intubation tube.

Figure 4:
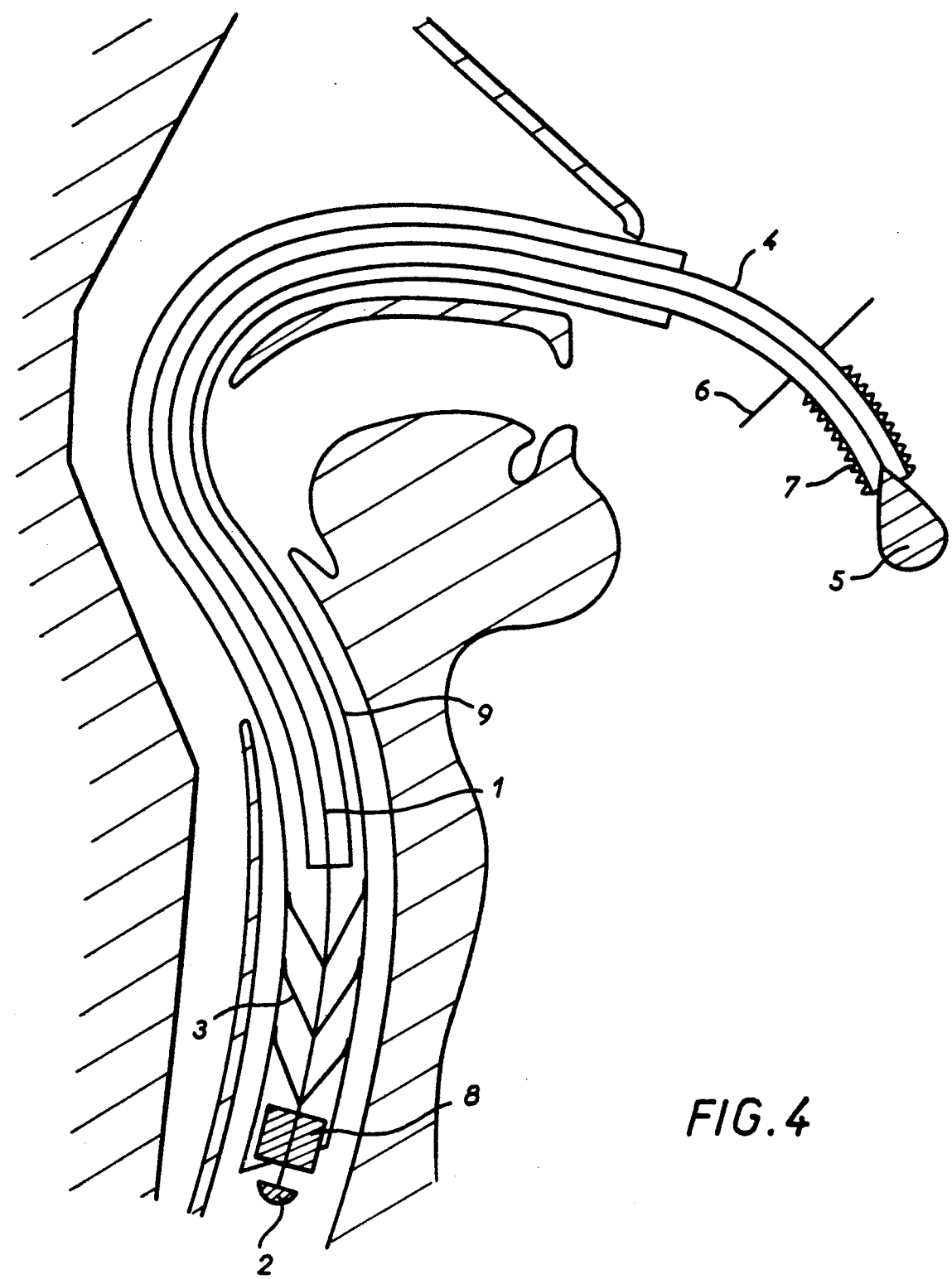
FIG. 4 is a view similar to that of FIG. 3, with the tube/cannula cleaning means in a deployed configuration.

FIG. 4 is a cross-section of the same embodiment of the device as in FIGS. 1, 2 and 3 in place in the intubated patient after introduction into the intubation tube (9) by the operator and after sliding the tube forwardly of the rod. The conformation of the device is that of FIG. 2: the collapsible system (3) and the foam cylinder (8) are released inside the intubation tube; the proximal end of the tube (4) abuts against the projection (5). The operator can then withdraw the device by holding it by the end (7), the rod (1) necessarily being withdrawn together with the tube (4) as the projection (5) is blocked against the proximal end of the tube (4). It is the withdrawal of the device by the operator that causes the intubation tube (9) to be brushed.

In the illustrated embodiment of FIG. 5 there is provided an inflatable balloon (18) between the collapsible system (3) and the distal end (2). The balloon (18) is in communication with a channel (20) running along the rod (1) and a piston inflator in the form of a syringe (19) is adapted to be connected to the enlarged proximal end (5) of the rod (1).

The device can be sterile, made of non-toxic materials and be supplied in a case.

The device can be disposable. It is recommended to use this device one to four times daily, depending on the patient.

We claim:

1. A device for preventing, by brushing, the blocking of intubation tubes in intubated patients or of tracheotomy cannulas in tracheotomized patients, the device comprising first and second elements each having a distal end adapted to be introduced into an intubation tube or into a tracheotomy cannula, and a proximal end adapted to be controlled by an operator, said first element comprising a flexible central rod, the distal end of said rod being rounded, retractable tube/cannula cleaning means being disposed around the rod in the vicinity of the distal end thereof, said second element comprising a flexible tube in which said first element is received and slidably movable, the retractable tube/cannula cleaning means having a retracted configuration when received inside said second element and a deployed configuration when released from said second element for cooperation with walls of the intubation tube or the tracheotomy cannula, said device being adapted to be inserted by its distal end into the intubation tube or the tracheotomy cannula of the patient, said flexible tube being slidable relative to said rod to release said retractable tube/cannula cleaning means into its deployed configuration.

2. A device according to claim 1, wherein said flexible tube comprises a locating stop for positioning the device in relation to the intubation tube or the tracheotomy cannula.

3. A device according to claim 1, wherein the proximal end of said flexible tube has a gripping portion.

4. A device according to claim 1, wherein the proximal end of said rod comprises an enlarged portion for gripping the same and abutting against said tube during the withdrawal of the device from the intubation tube or the tracheotomy cannula.

5. A device according to claim 1, wherein the retractable tube/cannula cleaning means comprises bristles projecting around said rod.

6. A device according to claim 5, wherein said bristles are at an angle to said central rod and directed toward the proximal end of said rod.

7. A device according to claim 1, wherein said retractable tube/cannula cleaning means comprises plastic strips attached to said rod and projecting therefrom.

8. A device according to claim 1, wherein a foam cylinder is mounted on said rod between said retractable tube/cannula cleaning means and the rounded distal end of said rod.

9. A device according to claim 1, wherein an inflatable balloon is disposed between said retractable tube/cannula cleaning means and said rounded distal end.

10. A device according to claim 1, wherein said device is disposable.

11. A device according to claim 1, wherein said second element is shorter than said first element.

12. A device according to claim 1, wherein an enlargement on the distal end of said rod is adapted to abut against the distal end of said tube when the rod is fully retracted into said tube.

* * * * *